United States Patent
Collinson et al.

(10) Patent No.: US 7,491,516 B2
(45) Date of Patent: Feb. 17, 2009

(54) DUAL SPECIFICITY ANTIBODIES AND METHODS OF MAKING AND USING

(75) Inventors: Albert Collinson, Marlboro, MA (US); George Avgerinos, Sudbury, MA (US); Richard Dixon, North Grafton, MA (US); Tariq Ghayur, Holliston, MA (US); Zehra Kaymakcalan, Westboro, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/894,550

(22) Filed: Jun. 28, 2001

(65) Prior Publication Data

US 2003/0040083 A1 Feb. 27, 2003

Related U.S. Application Data

(60) Provisional application No. 60/215,379, filed on Jun. 29, 2000.

(51) Int. Cl.
*C12P 21/08* (2006.01)
*C12P 21/04* (2006.01)
*C07K 16/00* (2006.01)
*A61K 39/00* (2006.01)
*A61K 39/395* (2006.01)

(52) U.S. Cl. .................. 435/70.21; 530/388.23; 424/130.1; 424/141.1; 424/142.1; 424/145.1

(58) Field of Classification Search ............. 530/388.1, 530/389.1, 351; 424/145.1, 158.1, 95.8, 424/85.2, 85.3, 189.1, 185.1
See application file for complete search history.

(56) References Cited

U.S. PATENT DOCUMENTS

| | | | |
|---|---|---|---|
| 5,168,062 A | 12/1992 | Stinski | |
| 5,179,017 A | 1/1993 | Axel et al. | |
| 5,580,717 A | 12/1996 | Dower et al. | |
| 5,622,701 A * | 4/1997 | Berg | 424/153.1 |
| 5,627,052 A | 5/1997 | Schrader et al. | |
| 5,756,095 A | 5/1998 | Juntila | |
| 5,885,793 A | 3/1999 | Griffiths et al. | |
| 5,939,598 A | 8/1999 | Kucherlapati et al. | |
| 5,969,108 A | 10/1999 | McCafferty et al. | |
| 6,036,978 A * | 3/2000 | Gombotz et al. | 424/491 |

FOREIGN PATENT DOCUMENTS

| | | | |
|---|---|---|---|
| EP | 218531 A * | 4/1987 | |
| EP | 436597 | 1/1989 | |
| EP | 589877 | 7/1991 | |
| WO | 92/01047 | 1/1992 | |
| WO | 92/02551 | 2/1992 | |
| WO | 92/09690 | 6/1992 | |
| WO | 92/20791 | 11/1992 | |
| WO | 97/08320 | 3/1997 | |
| WO | 97/29131 | 8/1997 | |
| WO | 98/201159 | 5/1998 | |
| WO | WO 98/20159 | 5/1998 | |
| WO | 98/31700 | 7/1998 | |
| WO | 98/47343 | 10/1998 | |
| WO | 98/49286 | 11/1998 | |
| WO | 99/36569 | 7/1999 | |
| WO | 99/45962 | 9/1999 | |
| WO | 00/56772 | 9/2000 | |

OTHER PUBLICATIONS

Kock et al., J. Exp. Med., 1986, vol. 163, No. 2, pp. 463-468.*
Miwa et al., Nature Medicine, 1998, vol. 4, No. 11, pp. 1287-1292.*
A_Geneseq_21 Database, Jan. 6, 2006, Result 4, AC No. AAP71394.*
Harlow et al., Eds. Antibodies, A Laboratory Manual, 1988 Cold Spring Harbor Lab. pp. 25, 42, 72, and 76.*
U.S. Appl. No. 60/126,603, filed Mar. 25, 1999, Salfeld et al.
Luger TA, Monoclonal Anti-IL 1 is directed against a common site of human IL 1α and IL β. (1986) Immunobiol., vol. 172, p. 346-356.
Karlin and Alschul Applications and statistics for multiple high-scoring segments in molecular sequences (1993) Proc. Natl. Acad. Sci USA 90:5873-77.
Altschul, et al. Basic local alignment search tool (1990) J. Mol. Biol. 215:403-10.
Altschul et al Gapped Blast and PSI-Blast: a new generation of protein database search programs (1997) Nucleic Acids Research 25(17):3389-3402.
Myers and Miller Optimal alignments in linear space (1988) Comput. Appl. Biosci. 4:11-17.
Jameson and Wolf The antigenic index: a novel algorithm for predicting antigenic determinants (1998) CABIOS, 4(1), 181-186.
Kohler and Milstein Continuous cultures of fused cells secreting antibody of predefined specificity (1975) Nature 256:495-497.
G. Galfre et al. Antibodies to major histocompatibility antigens produced by hybrid cell lines(1977) Nature 266:550-52.
Roes, J. et al. Mouse anti-mouse IgD monoclonal antibodies generated in IgD deficient mice.(1995) J. Immunol. Methods 183:231-237.
Lunn, M.P. et al. High-affinity anti-ganglioside IgG antibodies raised in complex ganglioside knockout mice; reexamination of GD1a Immunolocalization (2000) J. Neurochem. 75:404-412.

(Continued)

Primary Examiner—Gary B. Nickol
Assistant Examiner—Cherie M Woodward
(74) Attorney, Agent, or Firm—Tara Sashadri; Kenneth P. Zwicker

(57) ABSTRACT

Antibodies having dual specificity for two different but structurally related antigens are provided. The antibodies can be, for example, entirely human antibodies, recombinant antibodies, or monoclonal antibodies. Preferred antibodies have dual specificity for IL-1α and IL-1β and neutralize IL-1α and IL-1β activity in vitro and in vivo. An antibody of the invention can be a full-length antibody or an antigen-binding portion thereof. Methods of making and methods of using the antibodies of the invention are also provided. The antibodies, or antibody portions, of the invention are useful for detecting two different but structurally related antigens (e.g., IL-1α and IL-1β ) and for inhibiting the activity of the antigens, e.g., in a human subject suffering from a disorder in which IL-1α and/or IL-1β activity is detrimental.

25 Claims, No Drawings

OTHER PUBLICATIONS

MacQuitty, J.J. and Kay, R.M. GenPhrm's knockout mice (1992) Science 257:1188.

Lonberg, N. et al. Antigen-specific human antibodies from mice comprising four distinct genetic modifications. (1994) Nature 368:856-859.

Fishwild, D. M. et al. High-avidity human IgG kappa monoclonal antibodies from a novel strain of minifocus transgenic mice (1996) Nature Biotechnology 14:845-851.

Mendez, M. J. et al. Functional transplant of megabase human immunoglobulin loci recapitulates human antibody response in mice (1997) Nature Genetics 15:146-156.

Leader, K.A. et al. Antibody responses to the blood group antigen D in SCID mice econstituted with human blood monuclear cells. (1992) Immunology 76:229-234.

Bombil, F. et al. A promising model of primary human immunization in human -SCID mouse (1996) Immunobiol. 195:360-375.

Heard, C. et al. Two neutralizing human anti-RSV antibodies: cloning, expression, and characterization (1999) Molec. Med. 5:35-45.

Eren, R. et al. Human monoclonal antibodies specific to hepatitis B virus generated in a human/mouse ratiation chimera: the Trimera system (1998) Immunology 93:154-161.

Reisner, Y and Dagan, S. The Trimera mouse: generating human monoclonal antibodies and an animal model for human diseases (1998) Trends Biotechnol. 16:242-246.

Clackson et al. Making antibody fragment using phage display libraries(1991) Nature 352:624-628.

Gram et al. In vitro selection and affinity maturation of antibodies from a naïve combinatorial immunoglobulin library (1992) PNAS 89:3576-3580.

Barbas et al. Assembly of combinatorial antibody libraries on phage surfaces: The gene III site (1991) PNAS 88:7978-7982.

McCafferty et al. Phage antibodies: filamentous phage displaying antibody variable domains Nature (1990) 348:552-554.

Knappik et al. Fully synthetic human combinatorial antibody libraries (HuCAL) based on modular consensus frameworks and CDRs randomized with trinucleotides (2000) J. Mol. Biol. 296:57-86.

Bird et al. Single-chain antigen-binding protiens (1988) Science 242:423-426.

Huston et al. Protien engineering of antibody binding sites: recovery of specific activity in an anti-digoxin singel-chain Fv analogue produced in *Escherichia coli* (1988) Proc. Natl. Acad. Sci. USA 85:5879-5883.

Boss, M.A. and Wood, C. R. Genetically engineered antibodies (1985) Immunology Today 6:12-13).

Kaufman, R.J. and P.A. Sharp Amplification and expression of sequences contransfected with a modular dihydrofolate reductase complementary DNA gene (1982) Mol. Biol. 159:601-621.

Roberts, R.W. and Szostak, J.W. RNA-peptides fusions for the in vitro selection of peptides and proteins (1997) Proc. Natl. Acad. Sci. USA 94:1297-12302.

Babcock, J.S. et al. A novel strategy for generating monoclonal antibodies from single, isolated lymphocytes producing antibodies of defined specificities (1996) Proc. Natl. Acad. Sci. USA 93:7843-7848.

Holliger, P., et al. "Diabodies": small bivalent and bispecific antibody fragments (1993) Proc. Natl. Acad. Sci. USA 90:6444-6448.

Poljak, R.J., et al. Production and structure of diabodies (1994) Structure 2:1121-1123).

Albert, A.E et al. Time-dependent induction of protective anti-influenza immune responses in human peripheral blood lymphocyte/SCID mice (1997) J Immunol.;159(3):1393-1402.

Arai, K et al. An Elisa to determine the biodistribution of human monoclonal antibody in tumor-xenografted SCID mice (1998) J Immunol Method.;217(1-2):79-85.

Bocher, W.O. et al. Antigen specific B and T cells in human/mouse radiation chimera following immunizationin vivo (1999) Immunology; 96(4):634-41.

Chamat, S. et al. Human monoclonal antibodies isolated from spontaneous Epstein-Barr virus-transformed tumors of Hu-SPL-SCID mice and specific for fusion protein display broad neutralizing activity toward repiratory synytial virus (1999) J Infect Dis. ;180(2):268-77.

Gallo, M.L. et al.The human immunoglobulin loci introduced into mice: V (D) and J gene segments usage similar to that of adult humans. (2000) Eur J Immunol. :30:534-40.

Green, L.L. Antibody engineering via genetic engineering of the mouse: XenoMouse strains are a vehicle for the facile generation of therapeutic human monoclonal antibodies (1999) J Immunol Methods, 10;231(1-2):11-23.

Green, L.L. et al. Regulation of B cell development by variable gene complexity in mice reconstituted with human immunoglobulin yeast artificial chromosomes (1998) J Exp Med.;188(3)483-95.

Harding, F.A. et al. Class switching in human immunoglobulin transgenic mice (1995) Ann. NY Acad. Scii., 29;764:536-546.

Herz, U. et al. The humanized (Hu-PBMC) SCID mouse as an in vivo model for human IgE production and allergic inflammation of the skin (1997) Int Arch Allergy Immunol.;113(1-3):150-2.

Hutchins, W.A. et al. Human immune response to a peptide mimic of Neisseria menigtidis serogroup C in hu-PBMC-SCID mice (1999) Hybridoma;18(2):121-9.

Ilan, E. et al. The hepatitis B virus-trimera mouse: a model for human HBV infection and evaluation of anti-HBV therapeutic agents (1999) Hepatology;29(2):535-62.

Lonberg, N. Human antibodies from transgenic mice (1995) Int Rev Immunol.;13(1):65-93.

Murphy, W.J. et al. CD40 stimulation promotes human secondary immunogloulin responses in HuPBL-SCID chimeras (1999) Clin Immunol.;90(1):22-7.

Murphy, W.J. et al. The huPBL-SCID mouse as a means to examine human immune function in vivo (1996) Semin Immunol.; 8:233-41.

Nguyen, H. et al. Production of human monoclonal antibodies in SCID mouse (1997) Microbiol Immunol.;41(12);901-7.

Smithson, S.L. et al. Molecular analysis of the heavy chain of antibodies that recognize the capsular polysaccharide of Neisseria menigitidis in hum-PBMC reconstituted SCID mice and in the immunized human donor (1999) Mol Immunol.; 36:113-24.

Taylor, L.D. et al. A transgenic mouse that expresses a diversity of human sequence heavy and light chain immunoglobulins (1992) Nucleic Acids Res.;20(23):6287-95.

Yang, X.D. et al. Fully human anti-interleukin-8 monoclonal antibodies: potential therapeutics for the treatment of inflammatory disease states (1999) J Leukoc Biol.; 66(3):401-10.

Yoshinari, K. eta l. Differential effects of immunosuppressants and antibiotics on human monoclonal antibody production in SCID mouse ascites by five heterohybridomas (1998) Hydridoma;17(1):41-5.

Dinant, H J et al., "New Therapeutic Targets for Rheumatoid Arthritis," Pham World Sci, vol. 21, No. 2, 1999, pp. 49-59.

U.S. Appl. No. 12/006,068, filed Dec. 28, 2007, Chung-Ming Hsieh et al.

* cited by examiner

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: dual specificity antigen

<400> SEQUENCE: 1

Asn Glu Ala Gln Asn Ile Thr Asp Phe
1               5

<210> SEQ ID NO 2
<211> LENGTH: 18
<212> TYPE: PRT
<213> ORGANISM: Artificial Sequence
<220> FEATURE:
<223> OTHER INFORMATION: consensus sequence
```

```
<220> FEATURE:
<221> NAME/KEY: misc_feature
<222> LOCATION: (18)..(18)
<223> OTHER INFORMATION: Xaa is Pro or Gly

<400> SEQUENCE: 2

Met Ala Phe Leu Arg Ala Asn Gln Asn Asn Gly Lys Ile Ser Val Ala
1               5                   10                  15

Leu Xaa

<210> SEQ ID NO 3
<211> LENGTH: 16
<212> TYPE: PRT
<213> ORGANISM: Artificial Sequence
<220> FEATURE:
<223> OTHER INFORMATION: hybrid peptide

<400> SEQUENCE: 3

Thr Lys Gly Gly Gln Asp Ile Thr Asp Phe Gln Ile Leu Glu Asn Gln
1               5                   10                  15

<210> SEQ ID NO 4
<211> LENGTH: 153
<212> TYPE: PRT
<213> ORGANISM: Artificial Sequence
<220> FEATURE:
<223> OTHER INFORMATION: hybrid peptide

<400> SEQUENCE: 4

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
                20                  25                  30

Gly Gln Asp Met Glu Gln Gln Val Val Phe Ser Met Gly Ala Tyr Lys
            35                  40                  45

Ser Ser Lys Asp Asp Ala Lys Ile Thr Val Ile Leu Gly Leu Lys Glu
        50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser Ser
145                 150
```

DUAL SPECIFICITY ANTIBODIES AND METHODS OF MAKING AND USING

CROSS-REFERENCE TO RELATED APPLICATION

This application claims benefit of U.S. Provisional Application No. 60/215,379, filed Jun. 29, 2000.

BACKGROUND OF THE INVENTION

The mammalian immune system includes B lymphocytes that, in totality, express an antibody repertoire composed of hundreds of billions of different antibody specificities. A normal immune response to a particular antigen involves the selection from this repertoire of one or more antibodies that specifically bind the antigen, and the success of an immune response is based, at least in part, on the ability of these antibodies to specifically recognize (and ultimately eliminate) the stimulating antigen and "ignore" other molecules in the environment of the antibodies.

The usefulness of antibodies that specifically recognize one particular target antigen led to the development of monoclonal antibody technology. Standard hybridoma technology now allows for the preparation of antibodies having a single specificity for an antigen of interest. More recently, recombinant antibody techniques, such as screening of in vitro antibody libraries, have been developed. These techniques also allow for production of antibodies with a single specificity for an antigen of interest.

Antibodies having specificity for a single target antigen may, at least under certain circumstances, display undesired cross-reactivity or background binding to other antigens. This cross-reactivity or background binding, however, is usually unpredictable (i.e., it is not possible to predict which antigen the antibody will cross-react with). Moreover, it is usually distinguishable from specific antigen binding, since it typically represents only a very minor portion of the binding ability of the antibody (e.g., 1% or less of total antibody binding) and typically is only observed at high antibody concentrations (e.g., 1000 fold, or higher, concentrations than needed to observe specific antigen binding). Although there are several antigens that may belong to a structurally related family of proteins, the antibody response to a particular family member is highly specific. In addition, there are several examples of protein family members (e.g., members of the IL-1 and TNF families) that bind to the same receptor, receptor component or structurally related receptors, yet monoclonal antibodies raised against one member of the family do not show high cross reactivity towards other family members. There could be two reasons for this lack of cross-reactivity of MAbs towards various family members. First, in standard hybridoma production, one searches for only a few antibodies of high specificity/affinity for the target antigen and then checks for cross reactivity or background binding of the few selected antibodies. Second, although proteins within a family are structurally related, they may have exclusive, non-overlapping immunodominant epitopes. Therefore, MAbs raised by using full length protein may not cross react with other structurally related proteins.

There are also examples of monoclonal antibodies raised against an antigen of one species that will bind specifically to the same functional antigen in another species. For example, an anti-mouse X antibody may readily bind antigen X from human. This is because they share significant sequence and structural similarities though they are not identical. However, such species-cross-reactive antibodies do not constitute "dual specificity" antibodies, since they have specificity for the same antigen from different species.

Thus, monoclonal antibodies having predictable dual or multiple specificity, that is, antibodies having true specificity for two or more different antigens, are still needed.

SUMMARY OF THE INVENTION

This invention provides methods for making antibodies having dual specificity for at least two structurally-related, yet different, antigens. The method generally involves providing an antigen that comprises a common structural feature of the two different but structurally related molecules; exposing an antibody repertoire to the antigen; and selecting from the repertoire an antibody that specifically binds the two different but structurally related molecules to thereby obtain the dual specificity antibody. In clinical settings, several members of the same family of proteins may contribute to the various symptoms of a disease process. Therefore, use of a dual specificity antibody of the invention, which binds members of the same family of proteins, to block the functions of more than one member of the protein family can be beneficial for alleviating disease symptoms or for interrupting the disease process itself. Moreover, such dual specificity antibodies of the invention are useful to detect structurally related antigens, to purify structurally related antigens and in diagnostic assays involving structurally related antigens.

In a preferred embodiment, the antigen is designed based on a contiguous topological area of identity between the two different but structurally related molecules. For example, the two different but structurally related molecules can be proteins and the antigen can be a peptide comprising an amino acid sequence of a contiguous topological area of identity between the two proteins.

In another embodiment, the antigen is designed based on structurally mimicking a loop of a common fold of the two different but structurally related molecules. For example, the antigen can be a cyclic peptide that structurally mimics a loop of a common fold of two different but structurally related proteins.

In yet another embodiment, the antigen is designed based on splicing together alternating and/or overlapping portions of the two different but structurally related molecules to create a hybrid molecule. For example, the antigen can be a hybrid peptide made by splicing together alternating and/or overlapping amino acid sequences of two different but structurally related proteins.

In still another embodiment, the antigen can comprise one of the two different but structurally related molecules and the method involves selecting antibodies that specifically recognize both related molecules.

In the method of the invention, the antibody repertoire can be exposed to the antigen of interest either in vivo or in vitro. For example, in one embodiment, exposure of the repertoire to the antigen involves immunizing an animal in vivo with the antigen. This in vivo approach can further involve preparing a panel of hybridomas from lymphocytes of the animal and selecting a hybridoma that secretes an antibody that specifically binds the two different but structurally related molecules. The animal that is immunized can be, for example, a mouse, a rat, a rabbit, or a goat, or a transgenic version of any of the foregoing animals, such as a mouse that is transgenic for human immunoglobulin genes such that the mouse makes human antibodies upon antigenic stimulation. Other types of animals that can be immunized include mice with severe combined immunodeficiency (SCID) that have been reconstituted with human peripheral blood mononuclear cells (hu- PBMC-SCID chimeric mice) or lymphoid cells or precursors thereof and mice that have been treated with lethal total body irradiation, followed by radioprotection with bone marrow cells of a severe combined immunodeficiency (SCID) mouse, followed by engraftment with functional human lymphocytes (the Trimera system). Still another type of animal that can be immunized is an animal (e.g., mouse) whose genome has been "knocked out" (e.g., by homologous recombination) for an endogenous gene(s) encoding the antigen(s) of interest, wherein upon immunization with the antigen(s) of interest the KO animal recognizes the antigen(s) as foreign.

In another embodiment, the antibody repertoire is exposed to the antigen in vitro by screening a recombinant antibody library with the antigen. The recombinant antibody library can be, for example, expressed on the surface of bacteriophage or on the surface of yeast cells or on the surface of bacterial cells. In various embodiments, the recombinant antibody library is, for example, a scFv library or a Fab library. In yet another embodiment, antibody libraries are expressed as RNA-protein fusions.

Another approach to preparing the dual specificity antibodies involves a combination of in vivo and in vitro approaches, such as exposing the antibody repertoire to the antigen by in vivo immunization of an animal with the antigen, followed by in vitro screening of a recombinant antibody library prepared from lymphoid cells of the animal with the antigen. Still another approach involves exposing the antibody repertoire to the antigen by in vivo immunization of an animal with the antigen, followed by in vitro affinity maturation of a recombinant antibody library prepared from lymphoid cells of the animal. Yet another approach involves exposing the antibody repertoire to the antigen by in vivo immunization of an animal with the antigen, followed by selection of single antibody producing cells secreting an antibody of interest, recovery of heavy- and light chain variable region cDNAs from these selected cells (e.g., by PCR) and expression of the heavy- and light chain variable regions in mammalian host cells in vitro (referred to as the selected lymphocyte antibody method, or SLAM), thereby allowing for further selection and manipulation of the selection antibody gene sequences. Still further, monoconal antibodies can be selected by expression cloning by expressing heavy and light chain antibody genes in mammalian cells and selecting for mammalian cells secreting an antibody having the requisite binding specificity.

The methods of the invention allow for the preparation of various different types of dual specificity antibodies, including fully human antibodies, chimeric antibodies and CDR-grafted antibodies, and antigen-binding portions thereof. Dual specificity antibodies prepared according to the methods of the invention are also provided. A preferred dual specificity antibody of the invention is one that specifically binds interleukin-1α and interleukin-1β. Such a dual specificity antibody can be used in methods of detecting IL-1α or IL-1β comprising contacting IL-1α or IL-1β with the dual-specificity antibody, or antigen-binding portion thereof, such that IL-1α or IL-1β is detected. A neutralizing dual specificity antibody also can be used in methods of inhibiting IL-1α or IL-1β activity comprising contacting IL-1α or IL-1β with the dual-specificity antibody, or antigen-binding portion thereof, such that the activity of IL-1α or IL-1β is inhibited. Such dual specificity antibodies also can be used in methods of treating an interleukin-1-related disorder comprising administering to a subject suffering from an interleukin-1-related disorder the dual-specificity antibody, or antigen-binding portion thereof.

In another embodiment, the invention provides a method of making an antibody or an antigen binding portion thereof library by performing the following steps: a) obtaining a recombinant heavy chain or an antigen binding portion thereof library A from an antibody repertoire resulting from exposure to a first antigen; b) obtaining a recombinant light chain or an antigen binding portion thereof library B from an antibody repertoire resulting from exposure to the first antigen; c) obtaining a recombinant heavy chain or an antigen binding portion thereof library C from an antibody repertoire resulting from exposure to a second antigen; d) obtaining a recombinant light chain or an antigen binding portion thereof library D from an antibody repertoire resulting from exposure to the second antigen; and e) combining the recombinant heavy chain or an antigen binding portion thereof library A with the recombinant light chain or an antigen binding portion thereof library D to obtain an antibody or an antigen binding portion thereof library X and/or combining the recombinant heavy chain or an antigen binding portion thereof library C with the recombinant light chain or an antigen binding portion thereof library B to obtain an antibody or an antigen binding portion thereof library Y.

In another embodiment of the present invention, the immediately foregoing method of the invention can further comprise the step of combining the antibody or an antigen binding portion thereof library X with the antibody or an antigen binding portion thereof library Y to obtain an antibody or an antigen binding portion thereof library Z.

In a further embodiment, the present invention is directed to the antibody or an antigen binding portion thereof libraries X, Y and Z.

In another embodiment, the method of the present invention allows for the identification of dual specific antibody or an antigen binding portion thereof by selecting from the libraries X, Y and/or Z an antibody or an antigen binding portion thereof that binds both the first and the second antigen.

In a further embodiment, the present invention is directed to the dual specific antibody made and/or selected by any of the methods of the present invention.

In another embodiment, the present invention is also directed to the nucleotide sequence encoding each member of the antibody or an antigen binding portion thereof of libraries X, Y, and Z; and the dual specific antibody or an antigen binding portion thereof, a vector comprising the afore mentioned nucleotide sequences and host cell transfected with the afore mentioned vector.

In a preferred embodiment, the first and second antigen is each independently selected from the group consisting of proteins, polypeptides and peptides provided that the first and second antigens are not the same. In a further embodiment, the proteins, polypeptides and peptides are secreted proteins or surface receptors and the secreted protein is selected from the group consisting of an IFN, a TNF, an Interleukin, IP-10, PF4, a GRO, 9E3, EMAP-II, a CSF, an FGF, and a PDGF. In another preferred embodiment the first antigen is IL-1α and the second antigen is IL-1β.

DETAILED DESCRIPTION OF THE INVENTION

This invention pertains to the design and use of antigens for generating dual specificity antibodies, ie., antibodies having specificity for at least two different but structurally related molecules, as well as the selection, preparation and use of such dual specificity antibodies. The structural relatedness of the antigens of the invention can be over the entire antigen (e.g., protein) or only in certain structurally-related regions. The invention provides a method for obtaining a dual-specificity antibody that specifically binds two different but structurally related molecules, wherein the method involves:

providing an antigen that comprises a common structural feature of the two different but structurally related molecules;

exposing an antibody repertoire to the antigen; and selecting from the repertoire an antibody that specifically binds the two different but structurally related molecules to thereby obtain the dual specificity antibody.

It should be noted that while the invention is described herein in terms of recognition of two different but related antigens, it should be understood that the term "dual specificity antibody" is intended to include antibodies that specifically recognize even more than two different but related antigens, such as antibodies that recognize three, four, five or more structurally related but distinct antigens. Furthermore, the term "different but structurally related antigens" is intended to include antigens (e.g., proteins) whose overall structures are related as well as antigens (e.g., proteins) which share one or more structurally-related regions but that are otherwise unrelated. Thus, "different but structurally related" antigens could be, for example, two proteins that are members of the same protein family having a common overall structure or could be, for example, two proteins whose overall structure is disimilar (unrelated) but that each contain a structurally-related domain.

Various types of antigens may be used to elicit the antibodies of the invention and various methods of making antibodies can be applied to obtain a dual specificity antibody of the invention, as discussed in further detail below in the following subsections.

I. Dual Specificity Antigens

To prepare a dual specificity antibody of the invention, antibodies are raised against an antigen capable of eliciting dual specificity antibodies. Such antigens generally are referred to herein as dual specificity antigens. Various different types of dual specificity antigens can be used in the invention and the design of various types of dual specificity antigens is described further in the following subsections.

A. Contiguous Topological Areas

In one embodiment, a dual specificity antigen of the invention comprises a contiguous topological area of identity and/or similarity between the two different but structurally related molecules to which a dual specificity antibody is to be raised. Preferably, the antigen comprises the largest (e.g., longest) contiguous topological area of identity and/or similarity between the two different but structurally related molecules. Preferably, the two different but structurally related molecules are proteins and the dual specificity antigen comprises a linear peptide corresponding to the largest (e.g., longest) contiguous topological area of identity and/or similarity between the two proteins. The appropriate region of identity/similarity that is chosen is preferably a receptor or ligand binding region, although other regions of identity/similarity can also be used.

To determine contiguous topological areas of identity between two molecules (e.g., proteins), the two molecules (e.g., proteins) are compared (e.g., homology modeling, structural information or aligned) and identical or similar regions are identified. For proteins, an alignment algorithm can be used to create optimal alignment and identify the largest (e.g., longest) contiguous topological area of identity and/or similarity between the two proteins. A preferred, non-limiting example of a mathematical algorithm utilized for the comparison of two sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs of Altschul, et al. (1990) *J. Mol. Biol.* 215:403-10. To obtain gapped alignments for comparison purposes, Gapped BLAST can be utilized as described in Altschul et al., (1997) *Nucleic Acids Research* 25(17):3389-3402. When utilizing BLAST and Gapped BLAST programs, the default parameters of the respective programs (e.g., XBLAST and NBLAST) can be used. See http://www.ncbi.nlm.nih.gov. An alternative mathematical algorithm that can be used is that used in the ALIGN program described in Myers and Miller (1988) *Comput. Appi. Biosci.* 4:11-17.

When an appropriate region of identity/similarity is chosen, the dual specificity antigen corresponding to the region can be chemically synthesized. For example, for peptide antigens, the peptide can be synthesized by standard peptide synthesis methods. In one embodiment, the peptide antigen comprises L amino acids. In other embodiments, the peptide antigen may be partially or entirely composed of D amino acids. An example of the design of a dual specificity antigen based on a contiguous topological area of identity and/or similarity between two different but structurally related proteins is described in detail in Example 1.

B. Cyclic Peptides Mimicking a Structural Loop

In another embodiment, a dual specificity antigen of the invention comprises a cyclic molecule, preferably a cyclic peptide, that structurally mimics a key loop of a common fold of the two different but structurally related molecules (e.g., proteins) to which dual specificity antibodies are to be raised. To prepare this type of antigen, the structures of the two related molecules are compared and a loop of a common fold found in the two molecules is identified. Standard molecular modeling and crystallographic analysis can be used to aid in the identification of such loops and common folds. Identical and similar regions (e.g., amino acid sequences between two proteins) are identified and a consensus sequence can be designed for similar but not identical regions. A linear molecule, e.g., a linear peptide, is designed based on these similar and identical regions and this linear molecule can then be cyclized, by known chemical means, to create an antigen that mimics the key loop. For example, a proline and a glycine can be added to the end of a linear peptide to allow for cyclization of the peptide. An example of the design of a dual specificity antigen based on a cyclic peptide mimicking a structural loop shared by two different but structurally related proteins is described in detail in Example 2.

C. Hybrid Molecules

In another embodiment, a dual specificity antigen of the invention comprises a hybrid molecule, preferably a hybrid peptide, that includes alternating and/or overlapping regions of the two different but structurally related molecules (e.g., proteins) to which dual specificity antibodies are to be raised. To prepare this type of antigen, the structures of the two molecules are compared, and overlapping regions are identified (i.e., regions of identity), as well as nonidentical regions between the two molecules. A hybrid molecule (e.g., a hybrid peptide, when the two related molecules are proteins) is prepared that preferably comprises alternating regions (e.g., amino acid sequences) from each of the two molecules, as well as an overlapping region that is common to both molecules. Schematically, such a hybrid molecule can be described as: X-Y-Z, wherein Y represents a region of identity or strong similarity between the two related molecules (i.e, an overlapping region), X represents a region from one of the related molecules and Z represents a region from the other of the related molecules. An example of the design of a dual specificity antigen based on a hybrid peptide composed of sequences of two different but structurally related proteins is described in detail in Example 3.

Another type of hybrid molecule is one in which a peptide has been introduced into a full-length protein (referred to as a "target" protein). Peptides are selected that represent functional regions of two different but structurally related proteins, for example, receptor interacting regions. Such peptides are referred to herein as functional peptides. A functional peptide from one of the related proteins is then introduced into the full-length protein of the other related protein or, alternatively, an unrelated protein. For example, a peptide of IL-1α corresponding to a receptor interacting region of IL-1α is identified and this functional peptide of IL-1α is introduced into the full-length IL-1β protein to create a hybrid IL-1α/IL-1β molecule. Similarly, a peptide of IL-1β corresponding to a receptor interacting region of IL-1β is identified and this functional peptide of IL-1β is introduced into the full-length IL-1α protein to create a hybrid IL-1α/IL-1β molecule. This introduction of the functional peptide into the related full-length protein constrains the functional peptide at both ends and maintains the fold-structure of the functional peptide.

In case of an IL-1α/IL-1β hybrid, the functional peptide preferably is inserted (replaces the natural amino acids) in a target area representing the common fold structures of IL-1α and IL-1β. Such areas may be found over the entire length of the protein (e.g., in the N-terminal region, in the middle of the protein, in the C-terminal region). Furthermore, functional peptides representing the common IL-1α/IL-1β fold structures can also be inserted into an irrelevant protein, such as albumin or some other naturally occurring protein. In this instance, the preferred insertion site for the peptide is a region that allows the peptide to maintain the desired fold structure. Therefore, the insertion sites can be either at the N-terminus, the middle, or the C-terminus of the protein. The positioning of the peptide in any naturally occurring target protein is selected to mimic the structural constraints placed upon it by the native protein from which it is derived. While the functional peptide may simply be inserted into the target protein such that the amino acids of the functional peptide are added to the target protein, preferably the amino acids of the functional peptide replace a portion of the target protein into which it is inserted.

As a non-limiting example, a hybrid molecule is constructed for use as a dual specificity antigen for raising dual specificity antibodies to IL-1α and IL-1β wherein a functional peptide corresponding to a specific structural element of either IL-1α or IL-1β is introduced into the full length IL-1β or IL-1α in the equivalent structural position. The chosen hybrid molecule replaces residues 160-176 of IL-1β with residues 168-184 of IL-1α. The resulting molecule possesses the following amino acid sequence, in which the substituted IL-1α sequences (residues 168-184) are underlined:
APVRSLNCTLRDSQQKSLVMSGPYELKA-
LHLQGQDMEQQVVFSMGAYKSSKD DAK-
ITVILGLKEKNLYLSCVLKD-
DKPTLQLESVDPKNYPKKKMEKRFVFNKIEI
NNKLEFESAQFPNWYISTSQAENMPV-
FLGGTKGGQDITDFrMQFVSS (SEQ ID NO: 4)

This molecule can be prepared using standard molecular biology techniques (e.g., cloning, polymerase chain reaction) using the publicly available IL-1α and IL-1β cDNA sequences and recombinant protein expression techniques. A hybrid cDNA can be prepared, introduced into an appropriate expression vector and the polypeptide can be expressed by introducing the expression vector into an appropriate host cell.

D. Peptides Based on Hydrophobicity Plots

In another embodiment, a dual specificity antigen of the invention is selected based on hydrophobicity plots to select peptides predicted to be highly antigenic. For example, antigenic indexes of peptides can be calculated using computer software as described by Jameson and Wolf (CABIOS, 4(1), 181-186 (1988)) Regions of interest for antibody binding can be chosen to maximize the probability of antigenicity.

E. Immunization with Antigen-Transfected Cells

In another embodiment, a dual specificity antibody of the invention is prepared by immunization with antigen-transfected cells (i.e., dual specificity antigens of the invention can be antigen-transfected cells). Cell lines can be generated that stably express the two different but structurally related antigens, or a hybrid molecule thereof. For example, cell lines can be generated that stably express IL-1α or IL-1β or an IL-1α/IL-1β hybrid molecule (e.g., SEQ ID NO: 4). The molecules of interest can be secreted from the cells (in case of soluble proteins) or can be expressed on the cell surface (in case of receptors, enzymes). Gene delivery into the host cells to allow for expression of the antigens by the host cells can be accomplished by a number of conventional means, including but not limited to transfection, electroporation, cell fusion, lipofection, particle bombardment, microinjection, or viral infection. The cell lines expressing the antigens of interest can then be transplanted via one or more various routes (intraperitoneal, subcutaneous, intramuscular, and the like) into an animal of interest for antibody production. The cells then serve as a slow release source of the antigen of interest. Preferably the cells express the full length proteins. However, antigenic fragments can also be expressed. For soluble proteins, the proteins preferably are secreted by the cells. To generate a dual specificity antibody to the extracellular domain of two closely related receptors, the receptors preferably are expressed on the cell surface.

F. Immunization with One of the Structurally Related Molecules

In another embodiment, the dual specificity antigen is simply one of the two different but structurally related molecules to which dual specificity antibodies are to be raised. One of the two related molecules is used as the immunization agent and then the resultant antibody repertoire is screened for antibodies that bind, and more preferably neutralize, both of the two different but structurally related molecules. For example, one can immunize with either IL-1α or IL-1β and then screen for α/β binders, and more preferably neutralizers. As used in this embodiment, the term "immunize" is intended to broadly encompass the exposure of an antibody repertoire to the antigen, such as IL-1α or IL-1β, either in vivo or in vitro. Thus, this embodiment encompasses immunizing an animal with either IL-1α or IL-1β, and screening the resultant antibodies raised to select for those antibodies that bind both IL-1α and IL-1β, as well as screening a recombinant antibody library in vitro with either IL-1α or IL-1β and then selecting for recombinant antibodies that bind both IL-1α and IL-1β.

II. Methods of Making Dual Specificity Antibodies

To prepare a dual specificity antibody of the invention, an antibody repertoire (either in vivo or in vitro) is exposed to a dual specificity antigen, prepared as described in the previous section, and an appropriate dual specificity antibody is selected from the repertoire. The two elements of antibody recognition of an antigen are structural recognition and affinity maturation based on specific molecular interactions. During a natural immune response, low affinity antibodies that recognize structural motifs (for example the recognition of an antigen by certain pattern recognition receptors) are developed easily, and early on in the natural immune response this is followed by somatic mutations to increase the affinity of a few clones. Various in vivo and in vitro processes have been developed to mimic this natural phenomenon. Low affinity dual specificity antibodies can be generated by any of the in vitro and in vivo methods described herein and higher affinity dual specificity Mabs can be prepared by somatic mutagenesis methods described herein. Moreover, to optimize high affinity dual specificity MAbs, co-crystal structures of the low affinity MAbs with the desired antigens can be made. The structural information obtained can guide further affinity enhancements by altering (mutating) specific contact residues of the MAbs to enhance specific molecular interactions, as described herein.

Methods for making dual specificity antibodies using in vivo approaches, in vitro approaches, or a combination of both, are described in further detail in the following subsections.

A. In vivo Approaches

A standard in vivo approach to preparing antibodies is by immunizing an appropriate animal subject with an antigen to thereby expose the in vivo antibody repertoire to the antigen, followed by recovery of an antibody or antibodies of interest from the animal. Such an approach can be adapted to the preparation of dual specificity antibodies by use of a dual specificity antigen and selection for antibodies that specifically recognize the two structurally related molecules of interest. Dual specificity antibodies can be prepared by immunizing a suitable subject, (e.g., rabbit, goat, mouse or other mammal, including transgenic and knockout versions of such mammals) with an immunogenic preparation of a dual specificity antigen. An appropriate immunogenic preparation can contain, for example, a chemically synthesized or recombinantly expressed dual specificity antigen. The preparation can further include an adjuvant, such as Freund's complete or incomplete adjuvant, or similar immunostimulatory compound. Moreover, when used to raise antibodies, in particular by in vivo immunization, a dual specificity antigen of the invention can be used alone, or more preferably is used as a conjugate with a carrier protein. Such an approach for enhancing antibody responses is well known in the art. Examples of suitable carrier proteins to which a dual specificity antigen can be conjugated include keyhole limpet haemocyanin (KLH) and albumin.

Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes or lymph node cells or peripheral blood lymphocytes) from a mammal immunized with a dual specificity immunogen as described above, and the culture supernatants of the resulting hybridoma cells are screened to identify a hybridoma producing a monoclonal antibody with dual specificity for the two different but structurally related molecules of interest. Any of the many well known protocols used for fusing lymphocytes and immortalized cell lines can be applied for the purpose of generating dual specificity monoclonal antibodies (see, e.g., G. Galfre et al. (1977) *Nature* 266:550-52; Gefter et al. *Somatic Cell Genet.*, cited supra; lerner, *Yale J. Biol. Med.*, cited supra; Kenneth, *Monoclonal Antibodies*, cited supra). Moreover, the ordinary skilled artisan will appreciate that there are many variations of such methods, which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing monoclonal antibodies that specifically recognize the two structurally related molecules of interest are identified by screening the hybridoma culture supernatants for such antibodies, e.g., using a standard ELISA assay, to select those antibodies that specifically can bind the two related molecules.

Depending on the type of antibody desired, various animal hosts may be used for in vivo immunization. A host that itself expresses an endogenous version of the antigen(s) of interest can be used or, alternatively, a host can be used that has been rendered deficient in an endogenous version of the antigen(s) of interest. For example, it has been shown that mice rendered deficient for a particular endogenous protein via homologous recombination at the corresponding endogenous gene (i.e., "knockout" mice) elicit a humoral response to the protein when immunized with it and thus can be used for the production of high affinity monoclonal antibodies to the protein (see e.g., Roes, J. et al. (1995) *J. Immunol. Methods* 183:231-237; Lunn, M. P. et al. (2000) *J. Neurochem.* 75:404-412).

For production of non-human antibodies (e.g., against a human dual specificity antigen), various non-human mammals are suitable as hosts for antibody production, including but not limited to mice, rats, rabbits and goats (and knockout versions thereof), although mice are preferred for hybridoma production. Furthermore, for production of fully-human antibodies against a human dual specificity antigen, a host non-human animal can be used that expresses a human antibody repertoire. Such non-human animals include transgenic animals (e.g., mice) carrying human immunoglobulin transgenes, hu-PBMC-SCID chimeric mice, and human/mouse radiation chimeras, each of which is discussed further below.

Thus, in one embodiment, the animal that is immunized with a dual specificity antigen is a non-human mammal, preferably a mouse, that is transgenic for human immunoglobulin genes such that the non-human mammal (e.g., mouse) makes human antibodies upon antigenic stimulation. In such animals, typically, human germline configuration heavy and light chain immunoglobulin transgenes are introduced into animals that have been engineered so that their endogenous heavy and light chain loci are inactive. Upon antigenic stimulation of such animals (e.g., with a human antigen), antibodies derived from the human immunoglobulin sequences (i.e., human antibodies) are produced, and human monoclonal antibodies can be made from lymphocytes of such animals by standard hybridoma technology. For further description of human immunoglobulin transgenic mice and their use in the production of human antibodies see for example, U.S. Pat. No. 5,939,598, PCT Publication No. WO 96/33735, PCT Publication No. WO 96/34096, PCT Publication WO 98/24893 and PCT Publication WO 99/53049 to Abgenix Inc., and U.S. Pat. No. 5,545,806, No. 5,569,825, No. 5,625, 126, No. 5,633,425, No. 5,661,016, No. 5,770,429, No. 5,814,318, No. 5,877,397 and PCT Publication WO 99/45962 to Genpharm Inc. See also MacQuitty, J. J. and Kay, R. M. (1992) *Science* 257:1188; Taylor, L. D. et al. (1992) *Nucleic Acids Res.* 20:6287-6295; Lonberg, N. et al. (1994) *Nature* 368:856-859; Lonberg, N. and Huszar, D. (1995) *Int. Rev. Immunol.* 13:65-93; Harding, F. A. and Lonberg, N. (1995) *Ann. N.Y. Acad. Sci.* 764:536-546; Fishwild, D. M. et al. (1996) *Nature Biotechnology* 14:845-851; Mendez, M. J. et al. (1997) *Nature Genetics* 15:146-156; Green, L. L. and Jakobovits, A. (1998) *J. Exp. Med.* 188:483-495; Green, L. L. (1999) *J. Immunol. Methods* 231:11-23; Yang, X. D. et al. (1999) *J. Leukoc. Biol.* 66:401-410; Gallo, M. L. et al. (2000) *Eur. J. Immunol.* 30:534-540.

In another embodiment, the animal that is immunized with a dual specificity antigen is a mouse with severe combined immunodeficiency (SCID) that has been reconstituted with human peripheral blood mononuclear cells or lymphoid cells or precursors thereof. Such mice, referred to as hu-PBMC-SCID chimeric mice, have been demonstrated to produce human immunoglobulin responses upon antigenic stimulation. For further description of these mice and their use in antibody generation, see for example Leader, K. A. et al. (1992) *Immunology* 76:229-234; Bombil, F. et al. (1996) *Immunobiol.* 195:360-375; Murphy, W. J. et al. (1996) *Semin. Immunol.* 8:233-241; Herz, U. et al. (1997) *Int. Arch. Allergy Immunol.* 113:150-152; Albert, S. E. et al. (1997) *J. Immunol.* 159:1393-1403; Nguyen, H. et al. (1997) *Microbiol. Immunol.* 41:901-907; Arai, K. et al. (1998) *J. Immunol. Methods* 217:79-85; Yoshinari, K. and Arai, K. (1998) *Hybridoma* 17:41-45; Hutchins, W. A. et al. (1999) *Hybridoma* 18:121-129; Murphy, W. J. et al. (1999) *Clin. Immunol.* 90:22-27; Smithson, S. L. et al. (1999) *Mol. Immunol.* 36:113-124; Chamat, S. et al. (1999) *J. Infect. Diseases* 180:268-277; and Heard, C. et al. (1999) *Molec. Med.* 5:35-45.

In another embodiment, the animal that is immunized with a dual specificity antigen is a mouse that has been treated with lethal total body irradiation, followed by radioprotection with bone marrow cells of a severe combined immunodeficiency (SCID) mouse, followed by engraftment with functional human lymphocytes. This type of chimera, referred to as the Trimera system, has been used to produce human monoclonal antibodies by immunization of the mice with an antigen of interest followed by preparation of monoclonal antibodies using standard hybridoma technology. For further description of these mice and their use in antibody generation, see for example Eren, R. et al. (1998) *Immunology* 93:154-161; Reisner, Y and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

B. In vitro Approaches

Alternative to preparing dual specificity antibodies by in vivo immunization and selection, a dual specificity antibody of the invention can be identified and isolated by screening a recombinant combinatorial immunoglobulin library (e.g., an antibody phage display library) with a dual specificity antigen, to thereby isolate immunoglobulin library members that bind specifically to the two structurally related, but different, molecules of interest. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). In various embodiments, the phage display library is a scFv library or a Fab library. The phage display technique for screening recombinant antibody libraries has been described extensively in the art. Examples of methods and compounds particularly amenable for use in generating and screening antibody display library can be found in, for example, McCafferty et al. International Publication No. WO 92/01047, U.S. Pat. No. 5,969,108 and EP 589,877 (describing in particular display of scFv), Ladner et al. U.S. Pat. No. 5,223,409, No. 5,403,484, No. 5,571,698, No. 5,837,500 and EP 436,597 (describing, for example, pIII fusion); Dower et al. International Publication No. WO 91/17271, U.S. Pat. No. 5,427,908, U.S. Pat. No. 5,580,717 and EP 527,839 (describing in particular display of Fab); Winter et al. International Publication WO 92/20791 and EP 368,684 (describing in particular cloning of immunoglobulin variable domain sequences); Griffiths et al. U.S. Pat. No. 5,885,793 and EP 589,877 (describing in particular isolation of human antibodies to human antigens using recombinant libraries); Garrard et al. International Publication No. WO 92/09690 (describing in particular phage expression techniques); Knappik et al. International Publication No. WO 97/08320 (describing the human recombinant antibody library HuCal); Salfeld et al. International Publication No. WO 97/29131, describing the preparation of a recombinant human antibody to a human antigen (human tumor necrosis factor alpha), as well as in vitro affinity maturation of the recombinant antibody) and Salfeld et al. U.S. Provisional Application Ser. No. 60/126,603, also describing the preparation of a recombinant human antibody to a human antigen (human interleukin-12), as well as in vitro affinity maturation of the recombinant antibody)

Other descriptions of recombinant antibody library screenings can be found in scientific publications such as Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; McCafferty et al. *Nature* (1990) 348:552-554; and Knappik et al. (2000) *J. Mol. Biol.* 296:57-86.

Alternative to the use of bacteriophage display systems, recombinant antibody libraries can be expressed on the surface of yeast cells or bacterial cells. Methods for preparing and screening libraries expressed on the surface of yeast cells are described further in PCT Publication WO 99/36569. Methods for preparing and screening libraries expressed on the surface of bacterial cells are described further in PCT Publication WO 98/49286.

Once an antibody of interest has been identified from a combinatorial library, DNAs encoding the light and heavy chains of the antibody are isolated by standard molecular biology techniques, such as by PCR amplification of DNA from the display package (e.g., phage) isolated during the library screening process. Nucleotide sequences of antibody light and heavy chain genes from which PCR primers can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

Once DNA fragments encoding the VH and VL segments of the antibody of interest are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the recombinant antibodies, or antibody portions of the invention, DNAs encoding partial or full-length light and heavy chains, obtained as described above, can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr- CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

C. Combination Approaches

Dual specificity antibodies of the invention also can be prepared using a combination of in vivo and in vitro approaches, such as methods in which the dual specificity antigen is originally exposed to an antibody repertoire in vivo in a host animal to stimulate production of antibodies that bind the dual specificity antigen but wherein further antibody selection and/or maturation (i.e., improvement) is accomplished using one or more in vitro techniques.

In one embodiment, such a combination method involves first immunizing a non-human animal (e.g., a mouse, rat, rabbit, goat, or transgenic version thereof, or a chimeric mouse) with the dual specificity antigen to stimulate an antibody response against the antigen, following by preparation and screening of a phage display antibody library using immunoglobulin sequences from lymphocytes stimulated in vivo by exposure to the dual specificity antigen. The first step of this combination procedure can be conducted as described in subsection IIA above, while the second step of this procedure can be conducted as described in subsection IIB above. Preferred methodologies for hyperimmunization of non-human animals followed by in vitro screening of phage display libraries prepared from the stimulated lymphocytes include those described by BioSite Inc., see e.g., PCT Publication WO 98/47343, PCT Publication WO 91/17271, U.S. Pat. No. 5,427,908 and U.S. Pat. No. 5,580,717.

In another embodiment, a combination method involves first immunizing a non-human animal (e.g., a mouse, rat, rabbit, goat, or knockout and/or transgenic version thereof, or a chimeric mouse) with the dual specificity antigen to stimulate an antibody response against the antigen and selection of lymphocytes that are producing antibodies having the desired dual specificity (e.g., by screening hybridomas prepared from the immunized animals). The rearranged antibody genes from the selected clones are then isolated (by standard cloning methods, such as reverse transcriptase-polymerase chain reaction) and subjected to in vitro affinity maturation, to thereby enhance the binding properties of the selected antibody or antibodies. The first step of this procedure can be conducted as described in subsection IIA above, while the second step of this procedure can be conducted as described in subsection IIB above, in particular using in vitro affinity maturation methods such as those described in PCT Publication WO 97/29131 and PCT Publication WO 00/56772.

In yet another combination method, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, as applied to the dual specificity antibodies of the invention, a non-human animal (e.g., a mouse, rat, rabbit, goat, or transgenic version thereof, or a chimeric mouse) first is immunized in vivo with the dual specificity antigen to stimulate an antibody response against the antigen and then single cells secreting antibodies of interest, e.g., specific for the dual specificity antigen, are selected using an antigen-specific hemolytic plaque assay (e.g., the dual specificity antigen itself, or the structurally-related molecules of interest, are coupled to sheep red blood cells using a linker, such as biotin, thereby allowing for identification of single cells that secrete antibodies with the appropriate specificity using the hemolytic plaque assay). Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies having the desired dual specificity. The amplified immunoglobulin sequences further can be manipulated in vitro, such as by in vitro affinity maturation, as described above.

In another embodiment, the combination method to produce a dual specific antibody involves the following steps. A first non-human animal is immunized with a first antigen and a second non-human animal is immunized with a second different antigen, wherein preferably the second antigen is structurally similar to the first antigen, to stimulate an antibody response in vivo. A recombinant heavy chain library and a recombinant light chain library are constructed from antibody genes derived from the first non-human animal and the second non-human animal, respectively, as described in section IIB. The heavy chain library from the animal immunized with the first antigen is combined with the light chain library from the animal immunized with the second antigen to generate an antibody library X. Similarly, the heavy chain library from the animal immunized with the second antigen is combined with the light chain library from the animal immunized with the first antigen to generate an antibody library Y. Additionally, libraries X and Y can be combined to generate library XY. Dual specific antibodies that bind both first and second antigen can be identified and isolated from X, Y and/or XY libraries.

III. Characteristics of Dual Specificity Antibodies

The invention provides dual specificity antibodies, as well as antibody portions thereof, that can be prepared in accordance with the methods of the invention. Preferably, the antibodies, or portions thereof, are isolated antibodies. Preferably, the antibodies, or portions thereof, are neutralizing antibodies. The antibodies of the invention include monoclonal and recombinant antibodies, and portions thereof. In various embodiments, the antibody, or portion thereof, may comprise amino acid sequences derived entirely from a single species, such as a fully human or fully mouse antibody, or portion thereof. In other embodiments, the antibody, or portion thereof, can be a chimeric antibody or a CDR-grafted antibody or other form of humanized antibody.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion"), as used herein, refers to one or more fragments of a dual specificity antibody that retain the ability to specifically bind two different but structurally related antigens. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988)

Science 242:423-426; and Huston et al. (1988) *Proc. Natl. Acad. Sci. USA* 85:5879-5883) Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

An "isolated dual specificity antibody", as used herein, is intended to refer to an a dual specificity antibody that is substantially free of other antibodies having different antigenic specificities (e.g., an isolated antibody that specifically binds two different but structurally related antigens, or structurally-related regions of otherwise unrelated antigens, but that is substantially free of antibodies that specifically bind other unrelated antigens). Moreover, an isolated dual specificity antibody may be substantially free of other cellular material and/or chemicals.

A "neutralizing antibody", as used is intended to refer to an antibody whose binding to a particular antigen results in inhibition of the biological activity of the antigen. This inhibition of the biological activity of the antigen can be assessed by measuring one or more indicators of biological activity of the antigen using an appropriate in vitro or in vivo assay.

A "monoclonal antibody" as used herein is intended to refer to a hybridoma-derived antibody (e.g., an antibody secreted by a hybridoma prepared by hybridoma technology, such as the standard Kohler and Milstein hybridoma methodology). Thus, a hybridoma-derived dual specificity antibody of the invention is still referred to as a monoclonal antibody although it has antigenic specificity for more than a single antigen.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

The term "human antibody" refers to antibodies having variable and constant regions corresponding to, or derived from, human germline immunoglobulin sequences as described by, for example, Kabat et al. (See Kabat, et al. (1991) *Sequences of Proteins of Immunological Interest, Fifth Edition*, U.S. Department of Health and Human Services, NIH Publication No. 91-3242). The human antibodies of the invention, however, may include amino acid residues not encoded by human germline immunoglobulin sequences (e.g., mutations introduced by random or site-specific mutagenesis in vitro or by somatic mutation in vivo), for example in the CDRs and in particular CDR3.

Recombinant human antibodies of the invention have variable regions, and may also include constant regions, derived from human germline immunoglobulin sequences (See Kabat, E. A., et al. (1991) *Sequences of Proteins of Immunological Interest, Fifth Edition*, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis or backmutation or both.

The term "backmutation" refers to a process in which some or all of the somatically mutated amino acids of a human antibody are replaced with the corresponding germline residues from a homologous germline antibody sequence. The heavy and light chain sequences of a human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmuation may occur at any stage of antibody optimization.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of $V_H$ and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

One way of measuring the binding kinetics of an antibody is by surface plasmon resonance. The term "surface plasmon resonance", as used herein, refers to an optical phenomenon that allows for the analysis of real-time biospecific interactions by detection of alterations in protein concentrations within a biosensor matrix, for example using the BIACORE bioassay system (Pharmacia Biosensor AB, Uppsala, Sweden and Piscataway, N.J.). For further descriptions, see Jönsson, U., et al. (1993) *Ann. Bid. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The dual specificity antibodies of the invention are prepared using any of the various methods for preparing antibodies described in subsection II above. The dual specificity antibodies of the invention may be directed against essentially any structurally related antigens, although preferred dual specificity antibodies of the invention are those that specifically bind IL-1α and IL-1β, which can be prepared using a dual specificity antigen such as those described in Examples 1-4. Other structurally related antigens that can be applied to the current invention include but are not limited to caspase family members, cytokine families, such as IL-1 family members (e.g., IL-1/IL-18), TNF family members (e.g., TNFα/TNFβ), IL-6 family members, Interferons, TGFβ family members, EGF family members, FGF family members, PDGF family members, VEGF family members, Angiopoietin family members, Bone morphogenic proteins, secreted proteinases (metallo-proteinases), and cytokine receptor families, such as IL-1-receptor family members, TNF-receptors family members TGFβ receptor family members, EGF receptor family members, FGF receptor family members, PDGF receptor family members, VEGF receptor family members and Angiopoietin receptor family members.

The dual specificity antibodies of the invention may display equal binding activity toward the two different but structurally related antigens to which it binds or, alternatively, the dual specificity antibodies may bind more preferentially to one of the two antigens, yet still have specificity towards the two related antigens as compared to unrelated antigens. The binding activity of the dual specificity antibodies toward the structurally related antigens, as well as toward unrelated antigens, can be assessed using standard in vitro immunoassays, such as ELISA or BIACORE bioassay analysis. Preferably, the ratio of $K_d$ of antibody toward structurally unrelated antigens to the $K_d$ of antibody toward structurally related antigens should be at least 3, even more preferably the ratio should be at least 5, even more preferably the ratio should be at least 10, or even more preferably the ratio should be at least 50, 100, 200, 300, 400, 500, 600, 700, 800, 900 or 1000.

In quantitative terms, the difference between background binding and dual specificity is one of level or degree. For example, background binding is at a low level, e.g., less than 5%, more preferably less than 3% and most preferably, about 0.1-1% whereas specific cross-reactivity or dual specificity binding is at a higher level, e.g., greater than 1%, more preferably greater than 3%, even more preferably greater than 5% and even more preferably greater than 10%. Additionally, preferably the $IC_{50}$ of the dual specificity antibody for the target antigens is close to the $ED_{50}$s of the antigens in a given bioassay.

A dual specificity antibody, or antigen-binding portion thereof, of the invention is preferably selected to have desirable binding kinetics (e.g., high affinity, low dissociation, slow off-rate, strong neutralizing activity) for one, and more preferably both, of the antigens to which it specifically binds. For example, the dual specificity antibody, or portion thereof, may bind one, and more preferably both, of the structurally related antigens with a $k_{off}$ rate constant of $0.1 s^{-1}$ or less, more preferably a $k_{off}$ rate constant of $1 \times 10^{-2} s^{-1}$ or less, even more preferably a $k_{off}$ rate constant of $1 \times 10^{-3} s^{-1}$ or less, even more preferably a $k_{off}$ rate constant of $1 \times 10^{-4} s^{-1}$ or less, or even more preferably a $k_{off}$ rate constant of $1 \times 10^{-5} s^{-1}$ or less, as determined by surface plasmon resonance. Alternatively or additionally, a dual specificity antibody, or portion thereof, may inhibit the activity of one, and more preferably both, of the structurally related antigens with an $IC_{50}$ of $1 \times 10^{-6} M$ or less, even more preferably with an $IC_{50}$ of $1 \times 10^{-7} M$ or less, even more preferably with an $IC_{50}$ of $1 \times 10^{-8} M$ or less, even more preferably with an $IC_{50}$ of $1 \times 10^{-9} M$ or less, even more preferably with an $IC_{50}$ of $1 \times 10^{-10} M$ or less, or even more preferably with an $IC_{50}$ of $1 \times 10^{-11} M$ or less. Preferably, $IC_{50}$ should be measured using a sensitive bioassay where $IC_{50}$ values should be close to the $ED_{50}$ value of the antigen in that assay.

The invention also provides pharmaceutical compositions comprising a dual specificity antibody, or antigen-binding portion thereof, of the invention and a pharmaceutically acceptable carrier. The pharmaceutical composition of the invention can further comprise at least one additional therapeutic agent, e.g., one or more additional therapeutic agents for treating a disorder in which use of the dual specificity antibody is beneficial to amelioration of the disorder. For example, when the dual specificity antibody specifically binds IL-1α and IL-1β, the pharmaceutical composition can further include one or more additional therapeutic agents for treating disorders in which IL-1 activity is detrimental.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-1 activity is detrimental. For example, an anti-IL-1α/IL-1β dual specificity antibodies, or antibody portions, of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

IV. Uses of Dual Specificity Antibodies

Given their ability to bind two different but structurally related antigens, the dual specificity antibodies, or portions thereof, of the invention can be used to detect either or both of these antigens (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting an antigen in a biological sample comprising contacting a biological sample with a dual specificity antibody, or antibody portion, of the invention that specifically recognizes the antigen and detecting either the antibody (or antibody portion) bound to antigen or unbound antibody (or antibody portion), to thereby detect the antigen in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Alternative to labeling the antibody, the antigen(s) can be assayed in biological fluids by a competition radioimmunoassay utilizing antigen standards labeled with a detectable substance and an unlabeled dual specificity antibody specific for the antigen(s). In this assay, the biological sample, the labeled antigen standards and the dual specificity antibody are combined and the amount of labeled antigen standard bound to the unlabeled antibody is determined. The amount of antigen in the biological sample is inversely proportional to the amount of labeled antigen standard bound to the unlabeled antibody.

In a preferred embodiment, the dual specificity antibody specifically recognizes IL-1α and IL-1β and the foregoing detection methods are used to detect IL-1α and/or IL-1β. Accordingly, the invention further provides a method of detecting IL-1α or IL-1β in a biological sample or tissue comprising contacting the biological sample or tissue suspected of containing IL-1α or IL-1β with a dual-specificity antibody, or antigen-binding portion thereof, of the invention and detecting IL-1α or IL-1β in the biological sample or tissue. The biological sample can be, for example, an in vitro sample, such as a sample of cells, tissue or bodily fluid (e.g., blood, plasma, urine, saliva etc.). Moreover, the tissue detected can be tissue located in vivo in a subject, e.g., tissue visualized by in vivo imaging of the tissue (e.g., using a labeled antibody)

The dual specificity antibodies of the invention also can be used for diagnostic purposes. In one embodiment, an antibody of the invention is used in a diagnostic assay in vitro, such as in a laboratory test to detect the antigen(s) of interest or in a point of care test to detect the antigen(s) of interest. Examples of well-established in vitro assays utilizing antibodies include ELISAs, RIAs, Western blots and the like. In another embodiment, an antibody of the invention is used in a diagnostic assay in vivo, such as an in vivo imaging test. For example, the antibody can be labeled with a detectable substance capable of being detected in vivo, the labeled antibody can be administered to a subject, and the labeled antibody can be detected in vivo, thereby allowing for in vivo imaging.

Dual specificity antibodies of the invention that specifically recognize IL-1α and IL-1β can be used in diagnostic assays to detect IL-1α and/or IL-1β for diagnostic purposes, for example in a variety of inflammatory diseases and disorders, as well as in spontaneous resorption of fetuses. With regard to specific types of diseases and disorders, the dual specificity anti-IL-1α/IL-1β antibodies of the invention can be used for diagnostic purposes in any of the diseases/disorders described herein with regard to the therapeutic uses of such antibodies (see below), such as disorders in which IL-1 activity is detrimental, discussed further below.

The dual specificity antibodies and antibody portions of the invention preferably are capable of neutralizing, both in vitro and in vivo, the activity of the antigens to which they bind. Accordingly, such antibodies and antibody portions of the invention can be used to inhibit the activity of the antigens, e.g., in a cell culture containing the antigens or in human subjects or in other mammalian subjects having the antigens with which the dual specificity antibody of the invention reacts. In one embodiment, the invention provides a method for inhibiting antigen activity comprising contacting the antigen with a dual specificity antibody or antibody portion of the invention such that antigen activity is inhibited. In a preferred embodiment, the dual specificity antibody binds IL-1α and IL-1β and the method is a method for inhibiting IL-1α and/or IL-1β activity by contacting IL-1α and/or IL-1β with the dual specificity antibody, or portion thereof. The IL-1α and/or IL-1β activity can be inhibited, for example, in vitro. For example, in a cell culture containing, or suspected of containing, IL-1α and/or IL-1β, an antibody or antibody portion of the invention can be added to the culture medium to inhibit IL-1α and/or IL-1β activity in the culture. Alternatively, IL-1α and/or IL-1β activity can be inhibited in vivo in a subject.

In another embodiment, the invention provides a method for inhibiting antigen activity in a subject suffering from a disorder in which that antigen activity is detrimental. The invention provides methods for inhibiting antigen activity in a subject suffering from such a disorder, which method comprises administering to the subject a dual specificity antibody or antibody portion of the invention such that antigen activity in the subject is inhibited. Preferably, the antigen is a human antigen and the subject is a human subject. An antibody of the invention can be administered to a human subject for therapeutic purposes. Moreover, an antibody of the invention can be administered to a non-human mammal expressing an antigen with which the antibody binds for veterinary purposes or as an animal model of human disease. Regarding the latter, such animal models may be useful for evaluating the therapeutic efficacy of antibodies of the invention (e.g., testing of dosages and time courses of administration).

Preferably, the dual specificity antibody binds IL-1α and IL-1β and the method for inhibiting antigen activity in a subject is a method for inhibiting IL-1 activity in a subject, for example a subject suffering from a disorder in which IL-1 activity is detrimental. As used herein, the term "a disorder in which IL-1 activity is detrimental" is intended to include diseases and other disorders in which the presence of IL-1 (which encompasses both IL-1α and IL-1β) in a subject suffering from the disorder has been shown to be or is suspected of being either responsible for the pathophysiology of the disorder or a factor that contributes to a worsening of the disorder. Accordingly, a disorder in which IL-1 activity is detrimental is a disorder in which inhibition of IL-1 activity (i.e., either or both of IL-1α and IL-1β) is expected to alleviate the symptoms and/or progression of the disorder. Such disorders may be evidenced, for example, by an increase in the concentration of IL-1 in a biological fluid of a subject suffering from the disorder (e.g., an increase in the concentration of IL-1 in serum, plasma, synovial fluid, etc. of the subject), which can be detected, for example, using an anti-IL-1 antibody as described above.

Interleukin 1 plays a critical role in the pathology associated with a variety of diseases involving immune and inflammatory elements. These diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, diseases of the central nervous system (e.g., depression, schizophrenia, Alzheimers, Parkinsons, etc.), acute and chronic pain, and lipid imbalance. The human antibodies, and antibody portions of the invention can be used to treat humans suffering from autoimmune diseases, in particular those associated with inflammation, including, rheumatoid spondylitis, allergy, autoimmune diabetes, autoimmune uveitis.

Preferably, the IL-1α/IL-1β dual specificity antibodies of the invention or antigen-binding portions thereof, are used to treat rheumatoid arthritis, Crohn's disease, multiple sclerosis, insulin dependent diabetes, mellitus and psoriasis.

An IL-1α/IL-β dual specificity antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations which are part of this invention can be the antibodies of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen and COX-2 inhibitors. Other preferred combinations are corticosteroids including prednisolone; the well known side-effects of steroid use can be reduced or even eliminated by tapering the steroid dose required when treating patients in combination with the anti-IL-1 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-2, IL-6, IL-7, IL-8, IL-12, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (PCT Publication No. WO 97/29131), CA2 (Remicade™), CDP 571, CDP 870, Thalidamide and soluble p55 or p75 TNF receptors, derivatives, thereof, (p75TNFR1gG (Enbrel™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with IL-1 function; especially preferred are IL-12 and/or IL-18 antagonists including IL-12 and/or IL-18 antibodies or soluble IL-12 and/or IL-18 receptors, or IL-12 and/or IL-18 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R) and antiinflammatory cytokines (e.g. IL-4, IL-10, IL-11, IL-13 and TGFβ). Preferred combinations include methotrexate or leflunomide and in moderate or severe rheumatoid arthritis cases, cyclosporine.

Non-limiting examples of therapeutic agents for inflammatory bowel disease with which an antibody, or antibody portion, of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-2, IL-6, IL-7, IL-8, IL-12, IL-15, IL-16, IL-18, EMAP-II, GM-CSF, FGF, and PDGF. Antibodies of the invention can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFβ converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ).

Preferred examples of therapeutic agents for Crohn's disease in which an antibody or an antigen binding portion can be combined include the following: TNF antagonists, for example, anti-TNF antibodies, D2E7 (PCT Publication No. WO 97/29131), CA2 (Remicade™), CDP 571, TNFR-Ig constructs, (p75TNFRIgG (Enbrel™M) and p55TNFRIgG (Lenercept)) inhibitors and PDE4 inhibitors. Antibodies, or antigen binding portions thereof, of the invention or antigen binding portions thereof, can be combined with corticosteroids, for example, budenoside and dexamethasone, Antibodies of the invention or antigen binding portions thereof, may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. Antibodies of the invention or antigen binding portion thereof may also be used with T cell signaling inhibitors, for example, tyrosine kinase inhibitors 6-mercaptopurines. Antibodies of the invention or antigen binding portions thereof, can be combined with IL-11.

Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (Avonex; Biogen); interferon-β1b (Betaseron; Chiron/Berlex); Copolymer 1 (Cop-1; Copaxone; Teva Pharmaceutical Industries, Inc.); hyperbaric oxygen; intravenous immunoglobulin; clabribine; antibodies to or antagonists of other human cytokines or growth factors, for example, TNF, LT, IL-2, IL-6, IL-7, IL-8, IL-12, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, COX-2 inhibitors, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, IL-1 inhibitors, TNF inhibitors, and antibodies to CD40 ligand and CD80.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The present invention is further illustrated by the following examples which should not be construed as limiting in any way. The contents of all cited references, including literature references, issued patents, and published patent applications, as cited throughout this application are hereby expressly incorporated by reference.

EXAMPLE 1

Design of a Dual Specificity Antigen Based on a Contiguous Topological Area of Identity In this example, the largest contiguous topological area of identity between two different but structurally related proteins, IL-1α and IL-1β, was determined as a basis for designing a dual specificity antigen for raising dual specificity antibodies to IL-1α a and IL-1β. The BLAST algorithm was used to compare the two proteins and allows one to measure the tendency of one residue to replace another in similar structural or functional regions. This analysis allowed for the identification of the largest contiguous topological area of identity between IL-1α and IL-1β and to extend this area with any reasonable stretches of similarity to create a linear peptide that serves as a dual specificity antigen. The peptide that best fits these criteria has an amino acid sequence as follows:

```
NEAQNITDF          (SEQ ID NO: 1)
   * ****
```

The asterisk (*) indicates identical residues in both proteins and the other residues are strongly similar according to the BLAST algorithm. For example, lysine will often substitute for arginine in homologous proteins, but not for phenylalanine. This peptide of SEQ ID NO: 1 is a hybrid taken from two different sections of the structure which are running in opposite directions, so another reasonable representation of this epitope is:

dNdEdAdQNITDF (wherein the "d" prefix indicates that the amino acid residue is a D amino acid residue). Both the L amino acid version of the peptide and the version partially substituted with D amino acid residues are synthesized by standard chemical methods. The peptide is then conjugated to a carrier protein (e.g., KLH or albumin) and the conjugated peptide is used to select antibodies by in vitro or in vivo methods.

EXAMPLE 2

Design of a Dual Specificity Antigen Based on a Cyclic Peptide that Mimics a Loop of a Common Fold In this example, a cyclic peptide that structurally mimics a key loop of a common fold between two different but structurally related proteins, IL-1α and IL-1β, was constructed for use as a dual specificity antigen for raising dual specificity antibodies to IL-1α and IL-1β. The chosen loop represents residues 168-184 of IL-1α and residues 160-176 of IL-1 β. The consensus sequence is:

```
Cyclo-MAFLRANQNNGKISVAL(PG)     (SEQ ID NO: 2)
      *cbcccccccc**c*b*
```

The asterisk (*) indicates identical residues between IL-1α and IL-1β, c indicates consensus residues, i.e, residues similar to IL-1α and IL-1β but not actually present at this location in either protein, and b indicates there was no clear consensus residue so IL-1β sequence identity was retained. The linear peptide is synthesized by standard chemical synthesis methods. To cyclize this peptide, a proline and a glycine residue are added. The cyclic peptide may be synthesized using standard coupling conditions at high dilution in N,N-dimethylformamide (1 mg/ml). Prototypical reactions are run at room temperature using excess coupling reagent, such as benzotriazole-1-yl-oxy-tris-pyrrolidino-phosphonium hexafluoro phosphate (PyBOP; 2 eq) and sodium bicarbonate (10 eq). The peptide is then conjugated to a carrier protein (e.g., KLH or albumin) and the conjugated peptide is used to select antibodies by in vitro or in vivo methods.

EXAMPLE 3

Design of a Dual Specificity Antigen Based on a Hybrid Peptide

In this example, a hybrid peptide that includes alternating or overlapping sequences of two different but structurally related proteins, IL-1α and IL-1β, was constructed for use as a dual specificity antigen for raising dual specificity antibodies to IL-1α and IL-1β. To create the hybrid peptide, alternating and overlapping amino acid sequences of IL-1α and IL-1β were identified and spliced together to generate the following peptide:

```
    TKGGQDITDFQILENQ        (SEQ ID NO: 3)
    bbbbbbbbbb
         aaaaaaaaaa
```

The a and b indicate which protein is the source of the residues (a=IL-1α; b=IL-1β). The ITDF (SEQ ID NO: 4) motif common to both proteins was included in the hybrid peptide. Moreover, this hybrid peptide focuses on sequences from the carboxy termini of both proteins, which is known to be antigenic for neutralizing antibodies in both proteins as well. The hybrid peptide is synthesized by standard chemical synthesis methods. The peptide is then conjugated to a carrier protein (e.g., KLH or albumin) and the conjugated peptide is used to select antibodies by in vitro or in vivo methods.

EXAMPLE 4

Generation of Dual Specific antibodies to IL-1α and IL-1β

```
NEAQNITDF                      (SEQ ID NO: 1)

Cyclo-MAFLRANQNNGKISVAL(PG)    (SEQ ID NO: 2)

TKGGQDITDFQILENQ               (SEQ ID NO: 3)
```

Peptides of SEQ ID NO; 1, 2 and 3 were conjugated with KLH and individual rabbits were immunized. Antiserum from rabbits immunized with each of the three peptides showed good antibody response against the peptide used as antigen. However, only antiserum from rabbit immunized with Peptide of SEQ ID NO: 3 was able to bind both IL-1α protein and IL-1β protein.

Five mice (BA119-BA123) were immunized subcutaneously with peptide of SEQ ID NO: 3 conjugated with KLH plus Freund's incomplete adjuvant (FIA) once every three weeks for a total of three times, followed by two intravenous boosts with peptide of SEQ ID NO: 3 conjugated with KLH. Each mouse was bled 10 days after each immunization and antibody titer was determined by ELISA. Spleen cells from mouse BA119 and BA123 respectively were fused with myloma cell line P3X36Ag8.653 as described in section IIA, and the resulting fused cells were seeded one cell per well in several 96-well plates using limiting dilution. The hybridoma clones that grew were first assayed for IgG and IgM production by standard ELISA to identify antibody-producing clones. A total of 945 clones from mouse #BA123 fusion were isolated. Supernatants from 355 clones tested in an ELISA showed antigen binding activity to IL-1α, IL-1β or both IL-1α and IL-1β.

| # of clones | Antigen Specificity (against full length IL-1α and/or IL-1β) | Isotype |
| --- | --- | --- |
| 249 | IL-1 α only | IgG |
| 19 | IL-1 α only | IgM |
| 15 | IL-1 β only | IgG |
| 2 | IL-1 β only | IgM |
| 57 | IL-1 α and β | IgG |
| 13 | IL-1 α and β | IgM |

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A method of obtaining a dual-specificity antibody that specifically binds interleukin-1α and interleukin-1β, the method comprising:
   providing an antigen, wherein the antigen comprises the amino acid sequence TKGGQDITDFQILENQ (SEQ ID NO: 3);
   exposing an antibody repertoire to the antigen; and
   selecting from the repertoire an antibody that specifically binds IL-1α and IL-1β to thereby obtain the dual specificity antibody, wherein said dual-specificity antibody is not a fully mouse antibody.

2. The method of claim 1, wherein the antigen is designed based on a contiguous topological area of identity between IL-1α and IL-1β.

3. The method of claim 2, wherein the antigen comprises the amino acid sequence NEAQNITDF (SEQ ID NO: 1) or dNdEdAdQNITDF.

4. The method of claim 1, wherein the antigen is designed based on structurally mimicking a loop of a common fold of IL-1α and IL-1β.

5. The method of claim 4, wherein the antigen is a cyclic peptide comprising the amino acid sequence Cyclo-MAFL-RANQNNGKISVAL(PG) (SEQ ID NO: 2).

6. The method of claim 1, wherein the antigen comprises the amino acid sequence APVRSLNCTLRDSQQKSLVMS-GPYELKALIILQGQDMEQQVVFSM-GAYKSSKDDAKITVLLGL KEKNLYLSCVLKDDKPT-LQLESVDPKNYPKKKMEKRFVFN-KLEINNKLEFESAQFPNWYISTSQA ENMPVFLGGT-KGGQDITDFTMQFVSS (SEQ ID NO: 4).

7. The method of claim 1, wherein the antibody repertoire is exposed to the antigen in vivo by immunizing an animal with the antigen.

8. The method of claim 7, which further comprises preparing a panel of hybridomas from lymphocytes of the animal and selecting a hybridoma that secretes an antibody that specifically binds IL-1α and IL-1β.

9. The method of claim 7, wherein the animal is selected from the group consisting of mice, rats, rabbits and goats.

10. The method of claim 7, wherein the animal is a knockout mouse deficient for IL-1α, IL-1β or both IL-1α and IL-1β.

11. The method of claim 7, wherein the animal is a mouse that is transgenic for human immunoglobulin genes such that the mouse makes human antibodies upon antigenic stimulation.

12. The method of claim 7, wherein the animal is a mouse with severe combined immunodeficiency (SCID) that has been reconstituted with human peripheral blood mononuclear cells or lymphoid cells or precursors thereof.

13. The method of claim 7, wherein the animal is a mouse that has been treated with lethal total body irradiation, followed by radioprotection with bone marrow cells of a severe combined inimunodeficiency (SCID) mouse, followed by engraftment with functional human lymphocytes or precursors thereof.

14. The method of claim 1, wherein the antibody repertoire is exposed to the antigen in vitro by screening a recombinant antibody library with the antigen.

15. The method of claim 14, wherein the recombinant antibody library is expressed on the surface of bacteriophage.

16. The method of claim 14, wherein the recombinant antibody library is expressed on the surface of yeast cells.

17. The method of claim 14, wherein the recombinant antibody library is expressed on the surface of bacterial cells.

18. The method of claim 14, wherein the recombinant antibody library is expressed as RNA-protein fusions.

19. The method of claim 14, wherein the recombinant antibody library is a scFv library or a Fab library.

20. The method of claim 1, wherein the antibody repertoire is exposed to the antigen by in vivo immunization of an animal with the antigen, followed by in vitro screening of a recombinant antibody library prepared from lymphoid cells of the animal with the antigen.

21. The method of claim 1, wherein the antibody repertoire is exposed to the antigen by in vivo immunization of an animal with the antigen, followed by in vitro affinity maturation of a recombinant antibody library prepared from lymphoid cells of the animal.

22. The method of claim 1, wherein the antibody repertoire is exposed to the antigen by in vivo immunization of an animal with the antigen, followed by selection of single cells secreting antibodies that bind the antigen and recovery of heavy- and light-chain variable region cDNAs from the single cells.

23. The method of claim 1, wherein the dual-specificity antibody is a fully human antibody.

24. The method of claim 1, wherein the dual-specificity antibody is a chimeric antibody.

25. The method of claim 1, wherein the dual-specificity antibody is a CDR-grafted antibody.

* * * * *

UNITED STATES PATENT AND TRADEMARK OFFICE
CERTIFICATE OF CORRECTION

PATENT NO. : 7,491,516 B2
APPLICATION NO. : 09/894550
DATED : February 17, 2009
INVENTOR(S) : A. Collinson et al.

It is certified that error appears in the above-identified patent and that said Letters Patent is hereby corrected as shown below:

Column 37, line 25 to 31 claim 6 should read

6. The method of claim 1, wherein the antigen comprises the amino acid sequence APVRSLNCTLRDSQQKSLVMSGPYELKALHLQGQDMEQQVVFSMGAYKSSKD DAKITVILGLKEKNLYLSCVLKDDKPTLQLESVDPKNYPKKKMEKRFVFNKIEI NNKLEFESAQFPNWYISTSQAENMPVFLGGTKGGQDITDFTMQFVSS (SEQ ID NO:4).

Signed and Sealed this

Eighth Day of December, 2009

David J. Kappos
*Director of the United States Patent and Trademark Office*